United States Patent [19]
Milder et al.

[11] Patent Number: 5,281,213
[45] Date of Patent: Jan. 25, 1994

[54] CATHETER FOR ICE MAPPING AND ABLATION

[75] Inventors: Fredric L. Milder, Brookline, Mass.; A Ze'ev Hed, Nashua, N.H.

[73] Assignee: Implemed, Inc., Brookline, Mass.

[21] Appl. No.: 870,495

[22] Filed: Apr. 16, 1992

[51] Int. Cl.$^5$ ............................................. A61B 17/36
[52] U.S. Cl. ................................. 606/15; 606/33; 606/20; 609/95; 607/89; 607/105; 607/122; 607/154
[58] Field of Search ............ 606/15, 16, 17, 27, 606/28, 20-24; 128/702; 609/95

[56] References Cited

U.S. PATENT DOCUMENTS

| | | |
|---|---|---|
| 3,393,679 | 7/1968 | Crump et al. |
| 3,425,419 | 2/1969 | Dato |
| 3,512,531 | 5/1970 | Crump et al. |
| 3,548,829 | 12/1970 | Reynolds et al. |
| 3,664,344 | 5/1972 | Bryne |
| 3,823,718 | 7/1974 | Tromovitch |
| 3,859,986 | 1/1975 | Okada et al. |
| 3,910,277 | 10/1975 | Zimmer |
| 3,971,383 | 7/1976 | van Gerven |
| 4,029,102 | 6/1977 | Barger |
| 4,275,734 | 6/1981 | Mitchiner |
| 4,278,090 | 7/1981 | van Gerven |
| 4,406,656 | 9/1983 | Hattler et al. |
| 4,519,389 | 5/1985 | Gudkin et al. |
| 4,601,705 | 7/1986 | McCoy ................................. 604/95 |
| 4,641,649 | 2/1987 | Walinsky et al. ..................... 606/33 |
| 4,819,630 | 4/1989 | DeHart ................................. 606/15 |
| 4,832,024 | 5/1989 | Boussignac et al. ............. 606/15 X |
| 4,860,744 | 8/1989 | Johnson et al. |
| 4,895,741 | 2/1990 | Bentley et al. ....................... 606/27 |
| 4,934,340 | 6/1990 | Ebling et al. ...................... 604/95 X |
| 5,041,973 | 8/1991 | Lebron et al. .................... 128/642 X |
| 5,056,517 | 10/1991 | Fenici ................................ 128/786 X |
| 5,108,390 | 4/1992 | Potocky et al. |
| 5,147,355 | 9/1992 | Friedman et al. |
| 5,151,096 | 9/1992 | Khoury .............................. 606/17 X |
| 5,161,539 | 11/1992 | Evans et al. .................... 128/700 X |

FOREIGN PATENT DOCUMENTS

| | | |
|---|---|---|
| 2731651 | 1/1979 | Fed. Rep. of Germany. |
| 2477406 | 9/1981 | France. |
| WO8600232 | 1/1986 | PCT Int'l Appl. |
| 532976 | 11/1978 | U.S.S.R. |

*Primary Examiner*—Peter A. Achenbrenner
*Attorney, Agent, or Firm*—Weingarten, Schurgin, Gagnebin & Hayes

[57] ABSTRACT

The invention provides a catheter for ice mapping and ablation and a method of ablation using the catheter. The catheter includes at least two lumens for circulating a refrigerating fluid adjacent an ablation device located at the end of a catheter. The refrigerated ablation device is used to chill a localized region of myocardial tissue, thereby permitting the resulting change in electrical activity to be determined. In response to the test results, the ablation device may be used to make a lesion in the myocardial tissue to correct a cardiac arrhythmia. In one embodiment, the ablation device is an electrode which uses radio frequency energy to ablate the myocardial tissue. Alternatively, the ablation device is an electrode adapted for direct current ablation. In another embodiment, the electrode is replaced with an optical fiber in communication with a laser which uses the laser's light energy to ablate tissue. The embodiments may include provisions for steering the catheter and for stabilizing the ablation device at the proposed lesion site.

21 Claims, 5 Drawing Sheets

CATHETER FOR ICE MAPPING AND ABLATION

FIELD OF THE INVENTION

The invention relates to the field of catheters, and more particularly to a catheter used in cardiac procedures.

BACKGROUND OF THE INVENTION

Cardiac arrhythmias are caused by localized electrophysiologic phenomena. These are of generally two types: additional foci or reentrant circuits. Reentrant circuits can be highly localized, as in ventricular tachycardia postinfarction or AV node reentry, or can be of a grosser morphology, as in accessory pathway pathologies. Since they are localized phenomena, they can be treated surgically. The task is to remove or destroy the offending region, thereby eliminating the source of the arrhythmia.

Current surgical therapies include: cardiotomy; open chest cryoablation; closed-chest catheter radio frequency (rf) ablation; and closed-chest direct current ablation. Radio frequency catheter ablation is becoming the therapy of choice. The greatest drawback of rf ablation is that, prior to ablation, the site of the intended cardiac lesion must be determined by conventional electrocardiographic mapping. Unfortunately, conventional mapping does not provide definitive isolation of the problem area. In a great majority of cases, more than one lesion must be made in order to effect a cure. Multiple lesions are required because the effectiveness of each of the proposed lesion sites cannot be predetermined due to the limitations of conventional electrocardiographic mapping. Often five lesions, and sometimes as many as twenty lesions may be required before a successful result is obtained. Usually only one of the lesions is actually effective; the other lesions result in unnecessarily destroyed cardiac tissue.

Treatment of cardiac arrhythmias through selective ablation of cardiac tissue may be improved if, prior to ablation, the local electrical activity of the region can be suppressed to determine the effectiveness of the proposed lesion site in stopping the arrhythmia. Localized electrical activity may be suppressed by chilling small regions of myocardial tissue and then performing electrocardiographic mapping to evaluate the arrhythmia. This technique of cooling and mapping is called "zero-degree" or "ice" mapping. If the proposed lesion site would be effective, as determined by the ice mapping, to eliminate the arrhythmia, the site is ablated. Despite the advantages of cryoablation, it has not been the technique of choice for want of a single, easily operated device which effectively combines the functions of cryogenic cooling of cardiac tissue and tissue ablation.

SUMMARY OF THE INVENTION

The invention provides an ablation catheter which combines zero-degree or ice mapping and tissue ablation means in a single device. The invention includes a first and a second lumen for circulating a cooling fluid to the distal end of a catheter which includes an ablation device. The ablation device may be one pole of a multipole mapping electrode which conducts radio frequency energy, or direct current energy for tissue ablation. Alternatively, the ablation electrode may be replaced with an optical fiber in communication with a laser. The light energy is dispersed by a light diffuser toward a lesion site to ablate the tissue. The catheter may have an optional steering device to curve the distal end of the catheter, and the ablation device may be held in contact with the myocardial tissue with the aid of a pointed ridge.

Another feature of the invention is a method for ice mapping and ablation using the above-described catheter. The catheter is inserted into a cardiac vessel and placed against the site of a proposed lesion. Cooling fluid is circulated to the tip of the catheter through the lumens, thereby cooling a localized region of cardiac tissue. The electrical activity of the heart is then measured to evaluate the effectiveness of the proposed site. If the test results indicate that a lesion would eliminate a cardiac arrhythmia, the region is ablated with either radio frequency, direct current or laser light energy.

BRIEF DESCRIPTION OF THE DRAWINGS

A more complete understanding of the present invention and attendant advantages and features thereof will be more readily understood by reference to the following detailed description when considered in conjunction with the accompanying drawings wherein.

DETAILED DESCRIPTION OF THE INVENTION

Figure 1:
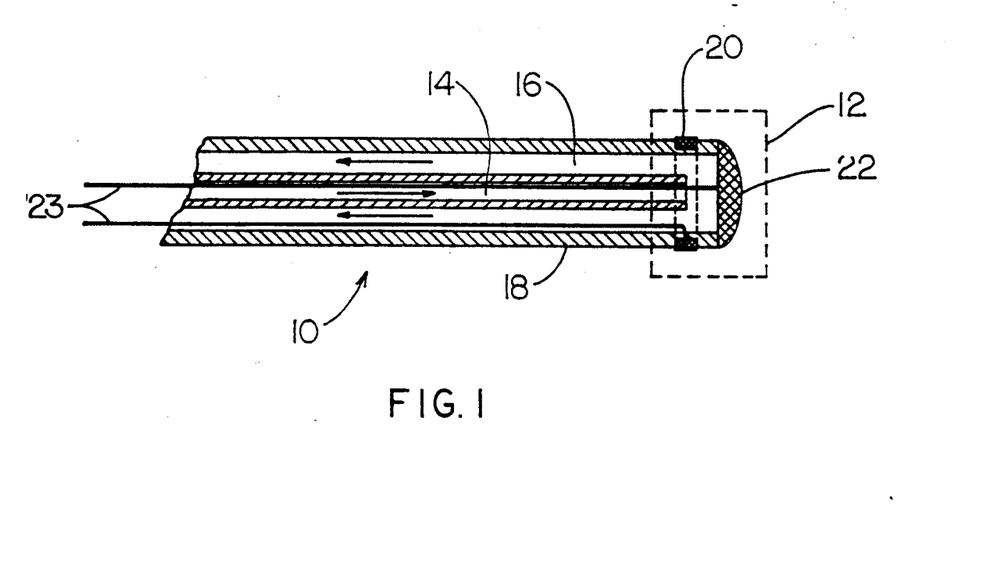
FIG. 1 is a schematic of an embodiment of the catheter of the invention for ice mapping and ablation, having mapping electrodes and a first rf ablation electrode at the distal end of the catheter.

FIG. 1 is a schematic of an embodiment of the ice mapping and ablation catheter 10. The catheter 10 has a tip 12 at its distal end which is alternately used for ice-mapping and radio frequency ablation. The proximal end of the catheter 10 is accessible to a surgeon and is connectable to a refrigerant source (not shown). The ice mapping and ablation catheter 10 combines two lumens 14 and 16 within the catheter body 18 to carry a refrigerant to and away from, respectively, the tip 12. The exemplary embodiment of the ice mapping and ablation catheter 10, depicted in FIG. 1, has the following wall dimensions for lumens 14 and 16: outer lumen 16, 0.117" Outer Diameter (O.D.) by 0.088" Inner Diameter (I.D.); and inner lumen 14, 0.068" O.D. by 0.060" I.D.

In the embodiment shown, the tip 12 includes a first electrode 20, circumferentially disposed on the catheter body 18, and a second electrode 22, both connected to an electrical signal amplifier with wires 23. The first and second electrodes 20 and 22 are used together to perform electrocardiographic mapping. The electrodes 20, 22 are made of an electrically conductive material such as copper, silver or aluminum, which is plated with gold, platinum or titanium. The second electrode 22 also acts as a thermal conductor between the catheter tip 12 and cardiac tissue when a refrigerant is passed through the inner lumen 14 to the tip 12. For radio frequency (rf) ablation, a wire 23 supplies (rf) current to the second electrode 22 which acts as an ablation device.

In other embodiments, additional electrodes may be added to the tip 12 to make a multipole mapping electrode. In another embodiment, a conductive refrigerant may be used to provide the electrical connection to the first electrode 20, thereby obviating the need for wires 23. In yet another embodiment, the refrigerant is an electrically insulating fluid like trimethylsiloxy terminated polydimethylsiloxane, and the wires 23, free of insulation, may be located within the lumens 14 and 16; one wire 23 in the inner lumen 14, and one wire 23 in the outer lumen 16. The combination of the insulating fluid and the insulating effect of the walls of the lumens 14 and 16 electrically isolate the wires 23 from each other.

In all of the embodiments, the ablation surface or device on the tip 12 is not necessarily the second electrode 22. The ablation device may be a separate surface which is distinguishable from the second electrode 22. In some embodiments, it may be desirable to entirely omit the first and second mapping electrodes 20 and 22 from the catheter 10, and to perform electrocardiographic mapping by other means, such as non-invasive cardiac monitoring.

Figure 2:
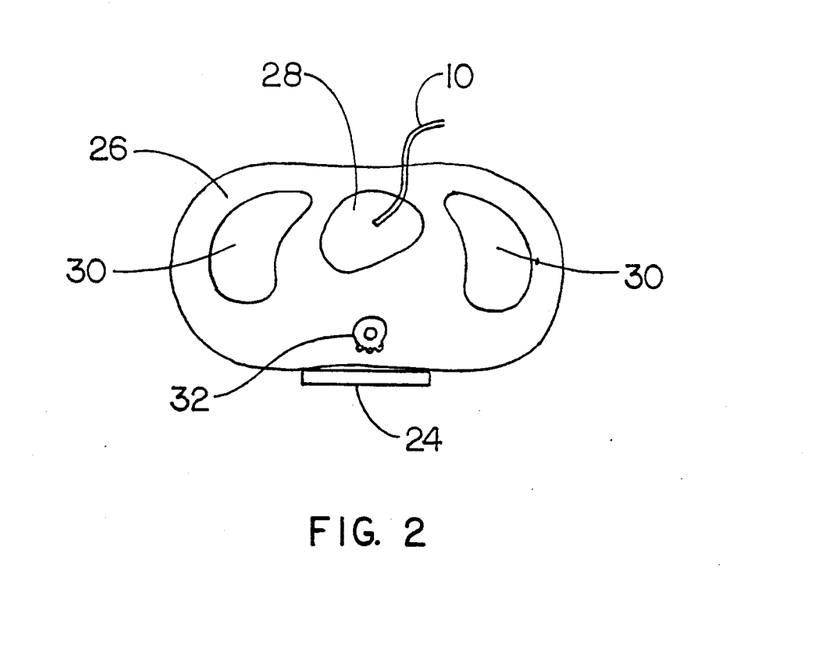
FIG. 2 is a cross-sectional view of a human body, showing a catheter of the invention within the heart and a second rf electrode beneath the body.
Figure 3:
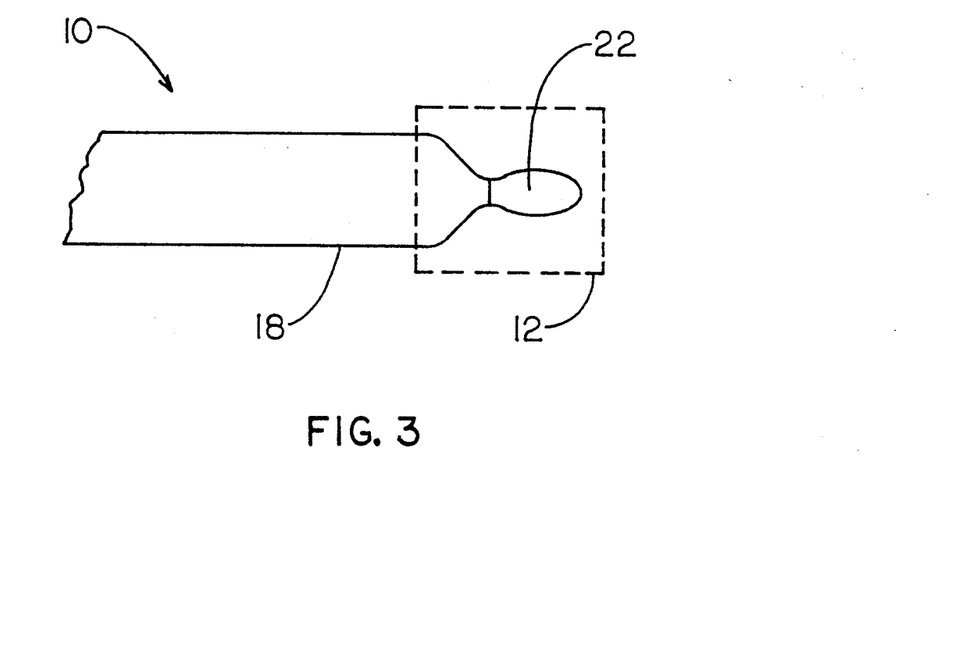
FIG. 3 is a side view of an embodiment of the catheter for ice mapping having an electrode for direct current ablation.

When the catheter 10 is used for ablation, the second electrode 22 and a third electrode 24, shown in FIG. 2, are employed. FIG. 2 is a representative cross-section of a human chest cavity 26 depicting approximate locations of a heart 28, lungs 30 and spinal column 32. The patient is shown resting on a conductive plate or third electrode 24. The ice-mapping and ablation catheter 10, which is smooth enough to pass easily through blood vessels and heart valves, is shown inside the heart 28. Creation of an electrical potential difference between the second electrode 22 and the third electrode 24 permits controlled ablation of cardiac tissue. The third electrode 24 may also be used for electrocardiographic mapping. In another embodiment of the catheter 10, shown in FIG. 3, a reconfigured tip 12 houses an elongated second electrode 22 useful for direct current ablation.

The catheter 10 of FIG. 1 is better understood with reference to its use in an operative procedure. Following the determination of a proposed lesion site by electrocardiographic mapping, using the first and second electrodes 20 and 22 with a method known in the art, the ice mapping and ablation catheter 10 is directed to the proposed region where lesions will be made. Following positioning of the tip 12 on the cardiac tissue, the refrigerant flow is turned on to allow a cooling fluid, such as ethyl alcohol, freon, or polydimethlsiloxane to flow from the reservoir within the inner lumen 14 to the tip 12, and then to return to the reservoir via the outer lumen 16. While the flow direction may be reversed, causing refrigerant to be introduced via the outer lumen 16 and withdrawn from the inner lumen 14, the resultant cooling of the exterior of the catheter body 18 would unnecessarily cool blood vessels and require that the refrigerant be colder when introduced into the catheter 10, to allow for warming of the coolant before it reaches the tip 12. In another embodiment of the catheter 10, the catheter body 18 may enclose a "bundle" of lumens as an alternative to the "tube-within-a-tube" configuration depicted in FIG. 1. In all of the configurations, circulation of refrigerant at the tip 12 permits controllable cooling of the tip 12 to cool the proposed lesion site.

Figure 4:
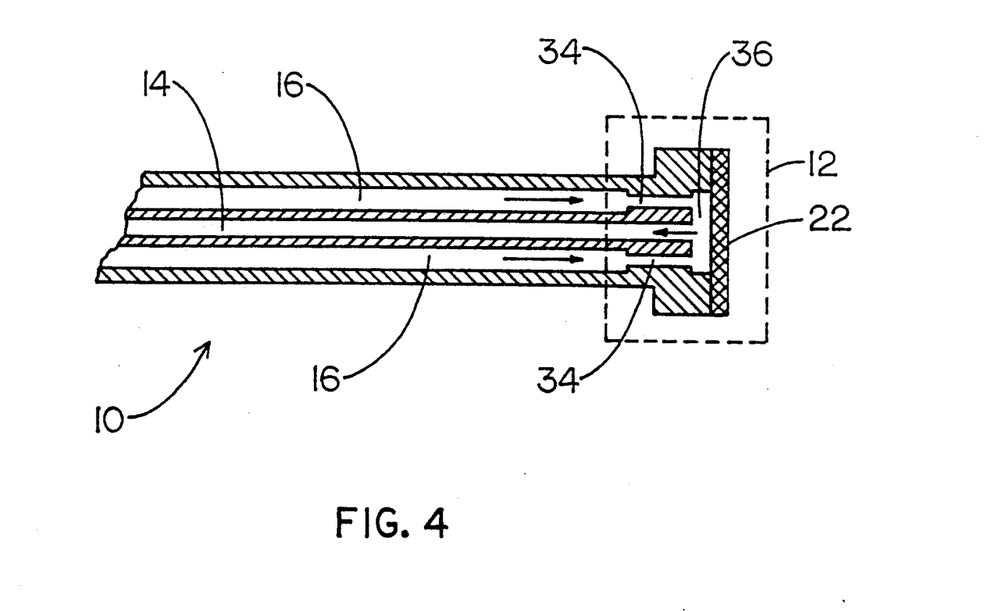
FIG. 4 is a schematic of an embodiment of the catheter for ice mapping and ablation having a tip which is cooled by gas expansion.

An alternative means of cooling the tip 12 is through gas expansion cooling by the Joule-Thompson effect, as i known in the art in cryoablation. A tip 12 configured for expansion cooling is shown in FIG. 4. The tip 12 has numerous small channels 34 which allow passage of a pressurized gas, such as nitrous oxide or carbon dioxide, from the outer lumen 16 into a gas expansion chamber 36. As the gas expands rapidly, it chills the thermally conductive electrode 22. The cold gas is then withdrawn from the tip 12 through the inner lumen 14. In lieu of pressurized gas, a liquid such as chlorodifluoromethane may be used for cooling. Liquids such as chlorodifluoromethane boil at a low temperature and cool by removing heat of vaporization through boiling.

Figure 5:
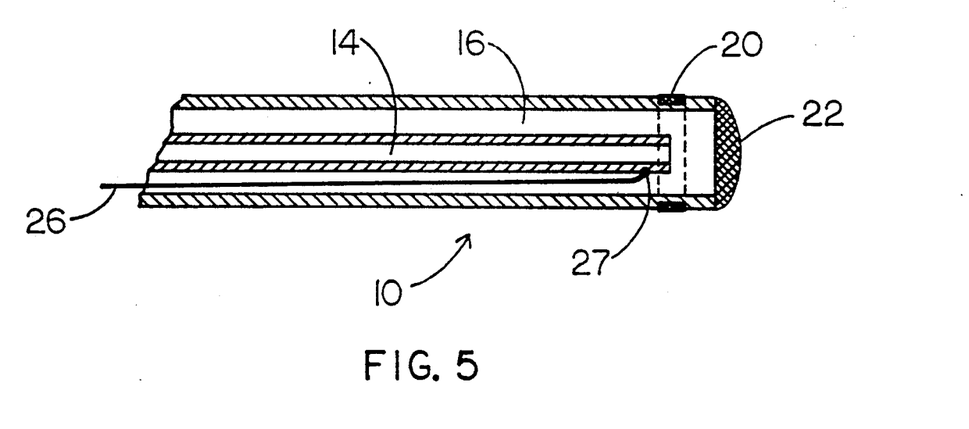
FIG. 5 is a schematic of an embodiment of the invention having a movable cable to permit steering of the catheter.

The exterior wall of the outer lumen 16 is the same surface as the exterior of the catheter body 18 and may include an internal metal braid to make the ice mapping and ablation catheter 10 torqueable for intracardiac manipulation. To further facilitate intracardiac manipulation, a cord, wire or cable 26 may be incorporated with, or inserted into, another lumen so as to make the ice mapping and ablation catheter 10 steerable. In the embodiment of FIG. 5, the cable 26 is attached to the inner lumen 14 at an attachment point 27 near the distal end of the inner lumen 14. When the surgeon tightens or pulls on the cable 26 the distal end of the inner lumen 14 moves within the outer lumen 16. As the distal end of the inner lumen 14 curves, it presses against the distal end of the outer lumen 16 and thereby causes the distal end of the catheter 10 to bend in proportion to the force applied to the cable 26. Conversely when the cable 2 is released, the curvature of the distal end of the catheter 10 is decreased.

Figure 6:
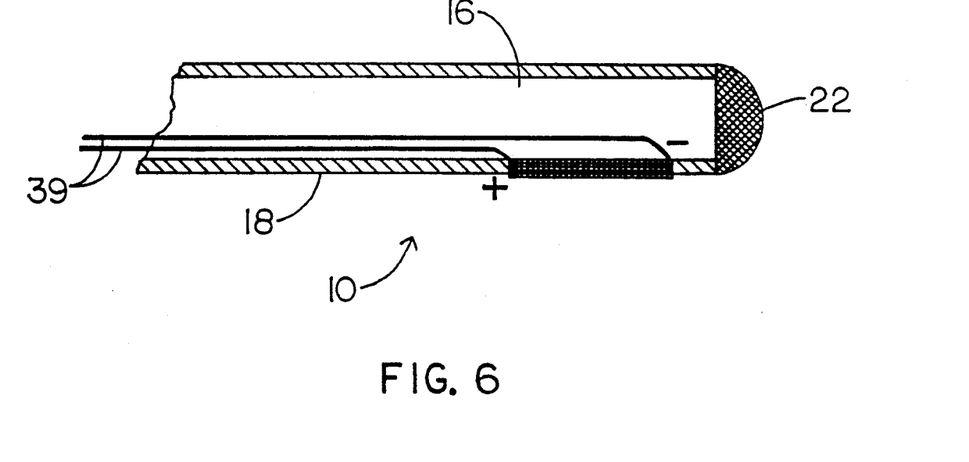
FIG. 6 is a schematic of an embodiment of the invention having a piezo-electric steering element within the catheter near the distal end.

It is further contemplated that a piezo-electric plastic, such as polyvinylidenefluoride (trade name Kynar ®), be added to the inner or outer surface of the distal end of either the inner lumen 14 or the outer lumen 16 to make the ice mapping and ablation catheter 10 similarly steerable. Referring to FIG. 6, a catheter 10 is shown with an approximately three centimeter Kynar ® segment 38 incorporated into a portion of the wall of the outer lumen 16 near the distal end of the catheter 10. The segment 38 has positive and negative electrical leads connected to an electrical power supply with wires 39. Application of an electric current of one polarity causes the segment 38 contract, which then causes the distal end of the outer lumen 16 to curve. Reversing the electrical polarity causes the segment 38 to expand, thereby causing the distal end of the outer lumen 16 to curve in the opposite direction. The movement of the outer lumen 16 causes a corresponding movement of the inner lumen 14 and permits controlled placement of the tip 12 against cardiac tissue.

It is further contemplated that a second segment 38 be incorporated into a wall portion of the outer lumen 16 opposite the first segment 38. Control of the distal end of the catheter 10 is achieved as with the single segment 38, except that voltages of opposite polarity are applied to the segments 38 simultaneously, thereby causing one segment 38 to contract and the other segment 38 to expand.

An ice mapping and ablation catheter 10, having the exemplary above-referenced wall dimensions and a length of 100 centimeters, requires refrigerant pressurization of approximately 200 pounds per square inch to produce a refrigerant flow of approximately 350 cc/min through the catheter 10. With a refrigerant inlet temperature of −60 degrees Celsius, a 350 cc/min flow, and a polyurethane wall material, the temperature of the tip 12 is approximately −10 degrees Celsius when the catheter body 18 is positioned inside a human body having a nominal temperature of 37 degrees Celsius. This temperature is sufficiently cold to do ice mapping.

Figure 7:
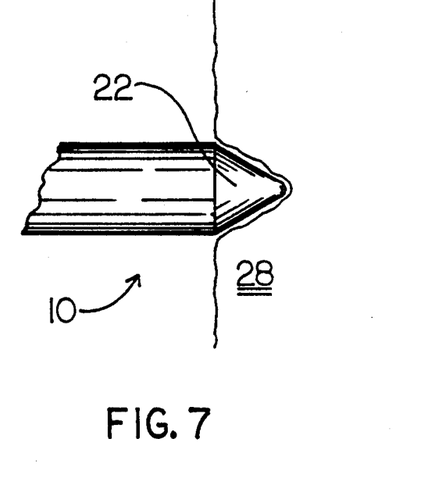
FIG. 7 illustrates an embodiment of a stabilization device having a point imbedded in cardiac tissue to temporarily anchor the ice mapping and ablation catheter at a desired location.
Figure 8:
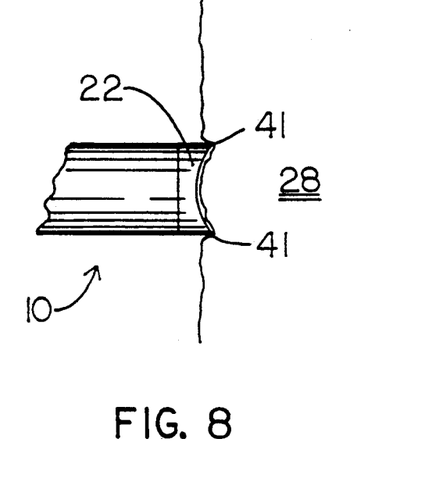
FIG. 8 illustrates another embodiment of a stabilization device having a concave electrode or ablation tip with a ridge on its perimeter.
Figure 9:
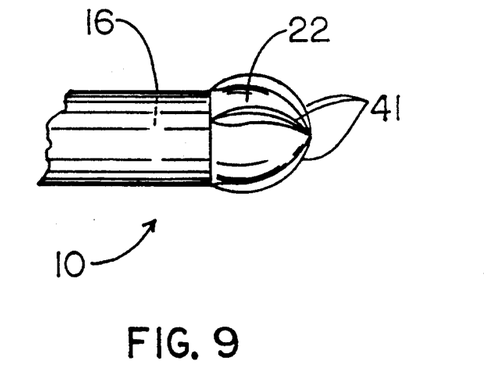
FIG. 9 illustrates another embodiment of a stabilization device which incorporates a series of longitudinal ridges on the tip of the catheter.
Figure 10:
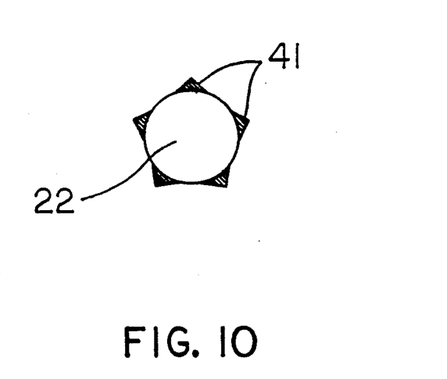
FIG. 10 is a cross-sectional view of the tip illustrated in FIG. 9, which more clearly illustrates the location and shape of the ridges.

The first step in the ice mapping procedure is placing the cooled tip 12 at the proposed lesion site. Because the operative procedure has several steps, he tip 12 must be stabilized at the proposed lesion site for the time necessary to ice map, to evaluate, and to ablate. A variety of configurations of the tip 12 may be employed to help secure or stabilize the catheter 10 in place against the myocardium. FIG. 7 depicts a pointed tip 12 or second electrode 22; FIG. 8 illustrates a concave tip 12 or second electrode 22 having lip or ridge 41; and FIG. 9 depicts a bulbous tip 12 having a series of ridges 41 on the side of the tip 12. FIG. 10 is a cross-sectional view of the tip 12 of FIG. 9, which more clearly illustrates the configuration of the stabilizing ridges 41.

When the cardiac tissue reaches approximately +5 degrees Celsius, its electrical activity is suppressed. If the proposed lesion site will be therapeutically effective when ablated, the arrhythmia will no longer be inducible once the electrical activity of the proposed site is suppressed by cooling. Having confirmed the effectiveness of the proposed site, rf ablation is performed using the second electrode 22 and the third electrode 24 in manner known to those skilled in the art.

Figure 11:
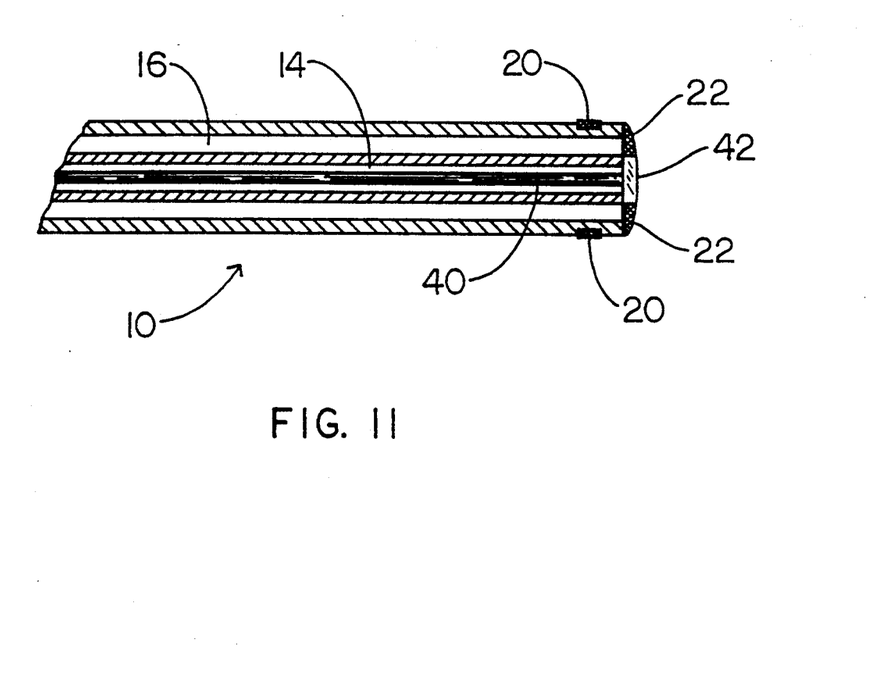
FIG. 11 is a schematic of an embodiment of the catheter of the invention with an optical fiber and light diffuser for laser ablation.
Figure 12:
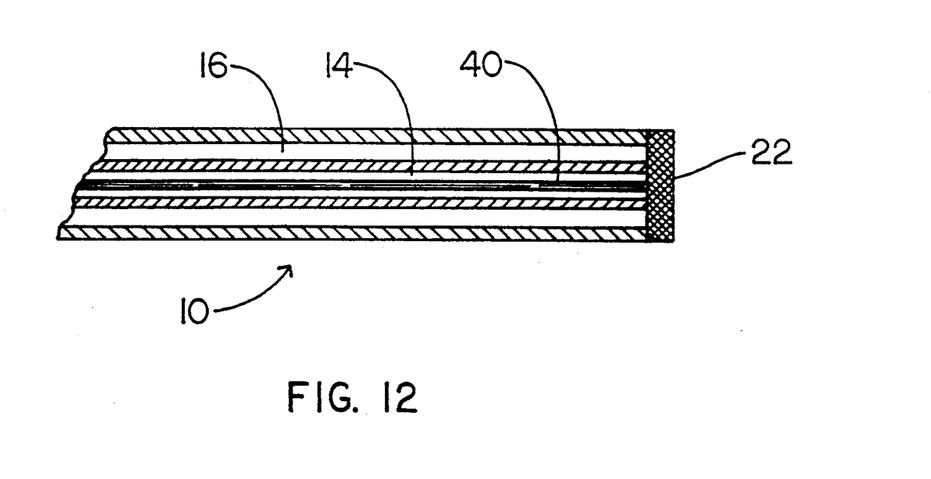
FIG. 12 is a schematic of an embodiment of the catheter of the invention having a heat ablation tip heated by laser energy.

FIG. 11 illustrates another embodiment of the catheter for ice mapping and ablation 10 which incorporates provisions for laser ablation. In this embodiment an optical fiber 40 is passed through the inner lumen 14 to a light diffuser 42 at the distal end of the catheter 10 in the center of the second electrode 22. The optical fiber 40 transmits light energy from a laser positioned at the proximal end of the optical fiber 40 at the proximal end of the catheter body 18. Because the laser light is highly collimated, the light diffuser 42 is used to enlarge the area ablated by the laser energy. Alternatively, the laser light may be used to heat the second electrode 22, as shown in FIG. 12, or a separate thermally conductive element, to a temperature of approximately +80 degrees Celsius for the procedure known as heat ablation. The ice-mapping and laser light or heat ablation procedure is similar to that for radio frequency or direct current ablation, the sole difference being the method of heat generation. As with rf ablation, the second electrode 22 may incorporate stabilization features as depicted in FIGS. 7-10.

The embodiment of FIG. 11 is shown configured with optional first and second electrodes 20 and 22 for electrocardiographic mapping, while the embodiment of FIG. 12 is not, to show the possible variety of configurations for the catheter 10. However, it is also contemplated that the catheter 10 of FIG. 12 be configured with mapping electrodes 20 and 22, and that the catheter 10 of FIG. 11 omit them.

A variety of modifications and variations of the present invention are possible in light of the above teachings. It is therefore to be understood that, within the scope of the appended claims, the present invention may be practiced otherwise than as specifically described hereinabove.

What is claimed is:

1. A catheter for ice mapping and ablation comprising:
   an open proximal end adapted for connection to a reservoir containing a cooling fluid;
   a closed, thermally conductive distal end;
   a first lumen conducting said cooling fluid from said proximal end to said distal end to chill cardiac tissue for suppression of localized electrical activity;
   a second lumen permitting return of said cooling fluid from said distal end to said proximal end;
   a non-cryogenic ablation means located at said distal end of said catheter for ablating myocardial tissue; and
   an electrocardiographic mapping means comprising at least one mapping electrode located near said distal end of said catheter.

2. A catheter for ice mapping and ablation having a proximal end and a distal end, said catheter comprising:
   a first lumen for permitting passage of an electrically conductive cooling fluid from said proximal end to said distal end;
   a second lumen permitting return of said cooling fluid from said distal end to said proximal end;
   an ablation means located near said distal end of said catheter for ablating myocardial tissue; and
   an electrocardiographic mapping means comprising at least one mapping electrode located near said distal end of said catheter, said electrocardiographic mapping means comprising at least one mapping electrode and wherein said cooling fluid is electrically conductive.

3. The catheter of claim 1, wherein said non-cryogenic ablation means comprises a first radio frequency electrode integral with said catheter cooperative with a second radio frequency electrode separated from said first electrode by tissue to be ablated, said first radio frequency electrode operative to transmit electric current from said first radio frequency electrode to said second radio frequency electrode.

4. The catheter of claim 1, wherein said non-cryogenic ablation means comprises an optical fiber extending from said proximal end to said distal end, said distal end of said optical fiber configured to permit passage of laser energy from said optical fiber axially outward from said distal end of said catheter through a light diffuser.

5. The catheter of claim 1, wherein said non-cryogenic ablation means comprises an optical fiber extending from said proximal end to said distal end of said catheter, said distal end comprising a heatable surface, said heatable surface heated by laser energy form said optical fiber.

6. A catheter for ice mapping and ablation having a proximal end and a distal end, said catheter comprising:
   a first lumen for permitting passage of a cooling fluid from said proximal end to said distal end;
   a second lumen permitting return of said cooling fluid from said distal end to said proximal end;
   an ablation means located near said distal end of said catheter for ablating myocardial tissue; and
   an expansion chamber located substantially at said distal end of said catheter, and
   wherein said cooling fluid is a pressurized gas which becomes cold upon expansion in an expansion chamber.

7. The catheter of claim 1, wherein said cooling fluid is a liquid.

8. The catheter of claim 7, wherein said liquid boils at a low temperature and cools by removing heat of vaporization through boiling.

9. The catheter of claim 8, wherein said liquid is chlorodifluoromethane.

10. The catheter of claim 1, further comprising a position stabilization means including at least one surface irregularity on said distal end to prevent slippage of said distal end when said distal end is in contact with a body tissue.

11. The catheter of claim 10, wherein said position stabilization means is a pointed conductive surface.

12. The catheter of claim 1, further comprising a catheter steering means.

13. The catheter of claim 12, wherein said catheter steering means comprises at least one flexible wire having a first end attached to said first lumen near said distal end of said catheter, and a second end detached from said catheter, accessible from said proximal end of said catheter, wherein increasing or reducing tension on said at least one flexible wire causes said distal end of said catheter to move.

14. The catheter of claim 12, wherein said catheter steering means comprising at least one segment of piezo-electric material anchored to a portion of said distal end of said catheter, wherein application of an electric voltage of a first polarity to said segment causes contraction of said segment and application of an electric voltage of a second polarity to said segment causes expansion of said segment, thereby causing said distal end of said catheter to move as a function of polarity and strength of said electric voltage.

15. A method of cryoablation comprising the steps of:
   introducing an ice mapping and ablation catheter into a cardiac blood vessel, said ice mapping and ablation catheter having a proximal end and a distal end, said ice mapping and ablation catheter comprising:
   a first lumen for permitting passage of a cooling fluid from said proximal end to said distal end;
   a second lumen permitting return of said cooling fluid from said distal end to said proximal end;
   an ablation means for ablating cardiac tissue;
   positioning said distal end of said catheter at a proposed lesion site;
   introducing a cooling fluid into said first lumen to cool said distal end and thereby cool said proposed lesion site to approximately +5 degrees Celsius;
   testing said proposed lesion site for electrical activity using electrocardiographic mapping means;
   evaluating results of said test to confirm effectiveness of said proposed lesion site; and
   generating a lesion by ablating said region with said ablation means.

16. The method of claim 15, wherein said generating said lesion by ablating uses radio frequency energy.

17. The method of claim 15, wherein said ice mapping and ablation catheter further comprises a fiber optic filament and said generating said lesion by ablating comprises transmitting light energy from a laser through said fiber optic filament to the proposed lesion site.

18. The method of claim 17, wherein said generating said lesion by ablating further comprises controllably dispersing said light energy to enlarge said lesion.

19. The method of claim 15, wherein said generating said lesion by ablating is by heating.

20. The method of claim 19, wherein said heating is by the application of direct current energy.

21. A catheter for ice mapping and ablation comprising:
   an open proximal end adapted for connection to a reservoir containing a cooling fluid;
   a closed, thermally conductive distal end;
   a first lumen conducting said cooling fluid from said proximal end to said distal end to chill cardiac tissue for suppression of localized electrical activity;
   a second lumen permitting return of said cooling fluid from said distal end to said proximal end;
   a first electrode located near said distal end of said catheter, wherein said first electrode is a first pole of an electrocardiographic mapping means;
   a second electrode located at said distal end of said catheter, wherein said second electrode is a second pole of said electrocardiographic mapping means and a radio frequency ablation means operative to transmit electric current form said first radio frequency electrode to a second radio frequency electrode separated from said first radio frequency electrode by tissue including tissue to be ablated;
   a position stabilization means including at least one surface section on said distal end adapted to prevent slippage of said distal end when said distal end is in contact with said tissue to be ablated; and
   a steering means to position said radio frequency ablation means.

* * * * *

UNITED STATES PATENT AND TRADEMARK OFFICE
CERTIFICATE OF CORRECTION

PATENT NO. : 5,281,213
DATED : Jan. 25, 1994
INVENTOR(S) : Fredric L. Milder, et al.

It is certified that error appears in the above-indentified patent and that said Letters Patent is hereby corrected as shown below:

Column 4, line 25, "i known" should read --is known--.

Column 4, line 53, "the cable 2" should read --the cable 26--.

Column 5, line 30, "he tip 12" should read --the tip 12---.

Column 8, line 48, "form" should read --from--.

Signed and Sealed this

Nineteenth Day of September, 1995

Attest:

BRUCE LEHMAN

Attesting Officer     Commissioner of Patents and Trademarks